US011272862B2

(12) United States Patent
Gu et al.

(10) Patent No.: US 11,272,862 B2
(45) Date of Patent: *Mar. 15, 2022

(54) ACTION RECOGNITION SYSTEM AND METHOD THEREOF

(71) Applicant: PIXART IMAGING INC., Hsin-Chu (TW)

(72) Inventors: Ren-Hau Gu, Hsin-Chu (TW); Chung-Wen Lo, Santa Clara, CA (US)

(73) Assignee: PIXART IMAGING INC., Hsin-Chu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/015,641

(22) Filed: Sep. 9, 2020

(65) Prior Publication Data

US 2020/0405196 A1   Dec. 31, 2020

Related U.S. Application Data

(63) Continuation of application No. 16/700,368, filed on Dec. 2, 2019, now Pat. No. 10,806,378, which is a (Continued)

(51) Int. Cl.
*A61B 5/11* (2006.01)
*A61B 5/00* (2006.01)
*A61B 5/024* (2006.01)

(52) U.S. Cl.
CPC .......... *A61B 5/1123* (2013.01); *A61B 5/1107* (2013.01); *A61B 5/0059* (2013.01); *A61B 5/02416* (2013.01); *A61B 5/681* (2013.01); *A61B 5/6824* (2013.01); *A61B 2562/0219* (2013.01)

(58) Field of Classification Search
CPC .......... A61B 5/00; A61B 5/11; A61B 5/1107; A61B 5/1123; A61B 5/0059; A61B 5/02416; A61B 5/024; A61B 5/681; A61B 5/6824; A61B 5/6825; A61B 5/6826; A61B 5/6828; A61B 5/6829; A61B 5/6801; A61B 5/6802; A61B 2562/0219; A61B 5/02427; A61B 5/02433; A61B 5/1125
See application file for complete search history.

(56) References Cited

U.S. PATENT DOCUMENTS 9,427,158 B2 *   8/2016   Choi ................... A61B 5/0082
10,019,078 B2 *   7/2018   Kim ..................... A61B 5/389
(Continued)

*Primary Examiner* — John R Lee
(74) *Attorney, Agent, or Firm* — Li & Cai Intellectual Property (USA) Office

(57) ABSTRACT

An action recognition system is illustrated. The action recognition system has an annular body, at least one light emitting unit, at least one light sensing unit and an action recognition module. The annular body is worn on a movable part of a user. One end of the light emitting unit is exposed on an inner side of the annular body, wherein the light emitting unit emits a first light beam illuminating at least a portion of the movable part. One end of the light sensing unit is exposed on the inner side of the annular body. The light sensing unit operatively senses a second light beam reflected by the at least portion of the movable part and generates a light sensing signal. The action recognition module is configured to operatively determine an action of the user according to the light sensing signal.

8 Claims, 9 Drawing Sheets

Related U.S. Application Data continuation of application No. 16/362,880, filed on Mar. 25, 2019, now Pat. No. 10,524,700, which is a continuation of application No. 14/686,974, filed on Apr. 15, 2015, now Pat. No. 10,285,627.

(56) References Cited

U.S. PATENT DOCUMENTS

| | | | | |
|---|---|---|---|---|
| 10,285,627 B2* | 5/2019 | Gu | | A61B 5/1107 |
| 10,524,700 B2* | 1/2020 | Gu | | A61B 5/1107 |
| 10,806,378 B2* | 10/2020 | Gu | | A61B 5/1107 |
| 2004/0064728 A1* | 4/2004 | Scheurich | | G06F 21/35 |
| | | | | 726/9 |
| 2010/0145171 A1* | 6/2010 | Park | | A61B 5/1455 |
| | | | | 600/324 |
| 2011/0054360 A1* | 3/2011 | Son | | A61B 5/1126 |
| | | | | 600/595 |
| 2011/0112793 A1* | 5/2011 | Diebold | | A61B 5/721 |
| | | | | 702/141 |
| 2011/0202306 A1* | 8/2011 | Eng | | A61F 4/00 |
| | | | | 702/150 |
| 2013/0129164 A1* | 5/2013 | Gu | | G06K 9/00013 |
| | | | | 382/124 |
| 2014/0055352 A1* | 2/2014 | Davis | | G06F 3/0304 |
| | | | | 345/156 |
| 2014/0062892 A1* | 3/2014 | Dickinson | | G06F 1/1643 |
| | | | | 345/173 |
| 2014/0073486 A1* | 3/2014 | Ahmed | | A61B 5/02427 |
| | | | | 482/9 |
| 2014/0085050 A1* | 3/2014 | Luna | | G07C 9/37 |
| | | | | 340/5.82 |
| 2014/0135631 A1* | 5/2014 | Brumback | | A61B 5/11 |
| | | | | 600/479 |
| 2014/0139637 A1* | 5/2014 | Mistry | | G06F 1/163 |
| | | | | 348/46 |
| 2014/0213863 A1* | 7/2014 | Loseu | | A61B 5/7207 |
| | | | | 600/324 |
| 2014/0257143 A1* | 9/2014 | Friedman | | A61B 5/1122 |
| | | | | 600/595 |
| 2014/0275852 A1* | 9/2014 | Hong | | A61B 5/0205 |
| | | | | 600/301 |
| 2014/0288436 A1* | 9/2014 | Venkatraman | | A61B 5/02416 |
| | | | | 600/479 |
| 2014/0368474 A1* | 12/2014 | Kim | | A61B 5/681 |
| | | | | 345/179 |
| 2015/0039880 A1* | 2/2015 | Aminzade | | H04W 4/023 |
| | | | | 713/100 |
| 2015/0062086 A1* | 3/2015 | Nattukallingal | | G06F 3/016 |
| | | | | 345/175 |
| 2015/0072619 A1* | 3/2015 | Abdurrahman | | H04W 4/80 |
| | | | | 455/41.2 |
| 2015/0084860 A1* | 3/2015 | Aleem | | G06F 3/014 |
| | | | | 345/156 |
| 2015/0109202 A1* | 4/2015 | Ataee | | G06F 3/014 |
| | | | | 345/156 |
| 2015/0140934 A1* | 5/2015 | Abdurrahman | | H04W 4/70 |
| | | | | 455/41.2 |
| 2015/0145673 A1* | 5/2015 | Choi | | A61B 5/389 |
| | | | | 340/539.12 |
| 2015/0148633 A1* | 5/2015 | Park | | A61B 5/0004 |
| | | | | 600/323 |
| 2015/0157220 A1* | 6/2015 | Fish | | A61B 5/14552 |
| | | | | 600/301 |
| 2015/0190062 A1* | 7/2015 | Han | | A61B 5/02416 |
| | | | | 600/479 |
| 2015/0262361 A1* | 9/2015 | Lo | | G06F 3/0312 |
| | | | | 382/103 |
| 2015/0297134 A1* | 10/2015 | Albert | | A61B 5/0205 |
| | | | | 600/384 |
| 2015/0301606 A1* | 10/2015 | Andrei | | G06F 3/011 |
| | | | | 345/156 |
| 2015/0305674 A1* | 10/2015 | McPherson | | A61B 5/4875 |
| | | | | 600/301 |
| 2015/0335283 A1* | 11/2015 | Fish | | A61B 5/02444 |
| | | | | 600/324 |
| 2015/0371028 A1* | 12/2015 | Patel | | G06F 21/34 |
| | | | | 726/16 |
| 2016/0012656 A1* | 1/2016 | Chuang | | G07C 9/25 |
| | | | | 340/5.52 |
| 2016/0038045 A1* | 2/2016 | Shapiro | | A61B 5/721 |
| | | | | 600/479 |
| 2016/0051158 A1* | 2/2016 | Silva | | A61B 5/721 |
| | | | | 600/479 |
| 2016/0051201 A1* | 2/2016 | Maani | | A61B 5/7278 |
| | | | | 600/301 |
| 2016/0058372 A1* | 3/2016 | Raghuram | | A61B 5/1112 |
| | | | | 600/595 |
| 2016/0062320 A1* | 3/2016 | Chung | | G06F 3/014 |
| | | | | 368/282 |
| 2016/0081627 A1* | 3/2016 | McGloin | | A61B 5/1123 |
| | | | | 600/301 |
| 2016/0089086 A1* | 3/2016 | Lin | | A61B 5/721 |
| | | | | 600/479 |
| 2016/0091980 A1* | 3/2016 | Baran | | G06F 1/163 |
| | | | | 345/156 |
| 2016/0096270 A1* | 4/2016 | Ibarz Gabardos | | B25J 9/161 |
| | | | | 700/253 |
| 2016/0120422 A1* | 5/2016 | Gu | | A61B 5/14551 |
| | | | | 600/479 |
| 2016/0150960 A1* | 6/2016 | Tsai | | A61B 5/0059 |
| | | | | 600/476 |
| 2016/0151668 A1* | 6/2016 | Barnes | | G06N 5/04 |
| | | | | 706/46 |
| 2016/0151672 A1* | 6/2016 | Barnes | | G06Q 30/02 |
| | | | | 434/247 |
| 2016/0157718 A1* | 6/2016 | Barnes | | A61B 5/02438 |
| | | | | 600/479 |
| 2016/0174856 A1* | 6/2016 | Huang | | A61B 5/7257 |
| | | | | 600/479 |
| 2016/0198995 A1* | 7/2016 | Yeung | | A61B 5/6826 |
| | | | | 600/595 |
| 2016/0213267 A1* | 7/2016 | Laakkonen | | A61B 5/02433 |
| 2016/0220130 A1* | 8/2016 | Han | | A61B 5/02416 |
| 2016/0305875 A1* | 10/2016 | Gu | | A61B 5/1107 |
| 2016/0345847 A1* | 12/2016 | Gu | | G06F 3/014 |
| 2019/0216369 A1* | 7/2019 | Gu | | A61B 5/1123 |
| 2020/0100708 A1* | 4/2020 | Gu | | A61B 5/1107 |
| 2020/0405196 A1* | 12/2020 | Gu | | A61B 5/1107 |

* cited by examiner

ACTION RECOGNITION SYSTEM AND METHOD THEREOF

CROSS-REFERENCE TO RELATED APPLICATIONS

This is a continuation application of U.S. application Ser. No. 16/700,368, filed on Dec. 2, 2019 and entitled "ACTION RECOGNITION SYSTEM AND METHOD THEREOF", which is a continuation application of U.S. application Ser. No. 16/362,880, filed on Mar. 25, 2019 and issued as U.S. Pat. No. 10,524,700 on Jan. 7, 2020 and entitled "ACTION RECOGNITION SYSTEM AND METHOD THEREOF", which is a continuation application of U.S. application Ser. No. 14/686,974 filed on Apr. 15, 2015 and issued as U.S. Pat. No. 10,285,627 on May 14, 2019 and entitled "ACTION RECOGNITION SYSTEM AND METHOD THEREOF", the entire disclosures of both are incorporated herein by reference.

BACKGROUND

1. Technical Field

The present disclosure relates to an action recognition system and method thereof in particular, to an action recognition system operable to determine an action of a user by optically detecting the muscular variation of a movable part of the user and the method thereof.

2. Description of Related Art

Muscle is one of the important tissues in the human body and mainly classifies into three types: skeletal muscle, smooth muscle, and cardiac muscle. The skeletal muscle mainly surrounds the extremities of the human body for controlling the basic body movement. More specifically, the contraction movements of the skeletal muscle are controlled by human conscious and stimulated by the never system in a manner that the contraction movements of the skeleton muscle can cause the movement of human skeleton helping the human body to move.

The surface electromyography (SEMG) is used to detect and record the electromyographic signals generated during the contraction movements of the muscle by electrodes placed on the surface above the muscle, wherein each of the electromyographic signals generated is related to a muscular activity and thus reflects the muscular variation during muscle movement. Currently the SEMG not only is utilized for medical diagnostic use but also is utilized for action recognition application.

However, existing SEMG still has issues with action recognition operations, such as the processing speed of a electromyographic signal processing apparatus does not easily comply to the requirements for action recognition due to the limitation of field programmable gate array (FPGA), the circuitry for amplifying the signal at sensing end is relatively complex, the measuring positions are limited only to the chest and forearms, particular hands, moreover electromyographic signals are vulnerable to interference of power source noises and electromagnetic noises. In other words, there still exist many issues with present action recognition systems using SEMG. To the rapidly developed wearable technology, action recognition products using electromyographic signals are still not suitable for consumer wearable electronic product applications.

SUMMARY

An exemplary embodiment of the present disclosure provides an action recognition system, and the action recognition system includes an annular body, at least one light emitting unit, at least one light sensing unit, and action recognition module. The annular body is configured to be worn on a movable part of a user. One end of the light emitting unit is exposed on an inner side of the annular body. The light emitting unit is operable to emit a first light beam illuminating at least a portion of the movable part. One end of the light sensing unit is exposed on the inner side of the annular body. The light sensing unit is operable to sense a second light beam reflected by the at least a portion of the movable part for generating a light sensing signal. The action recognition module is operable to identify and determine an action of the user according to the light sensing signal.

An exemplary embodiment of the present disclosure provides an action recognition method for an action recognition system. The action recognition system includes an annular body, at least one light emitting unit, at least one light sensing unit, and an action recognition module, wherein the annular body is configured to be worn on a movable part of a user. The action recognition method includes the following steps. The light emitting unit is first arranged to operatively emit a first light bean onto at least a portion of the movable part, wherein one end of the light emitting unit is disposed on an inner side of the annular body. Next, the light sensing unit is arranged and configured to sense a second light beam reflected by the at least a portion of the movable part and generate a light sensing signal, accordingly, wherein one end of the light sensing unit is disposed on the inner side of the annular body. Then, the action recognition module is driven to determine an action of the user according to the light sensing signal.

To sum up, exemplary embodiments of the present disclosure provides an action recognition system and method thereof, which are operable to generate a sensing signal responsive to the muscular variation of a user using optical sensing technique and eliminate the impact of EMI interference and power source noises. Moreover, the number of muscle measuring or detection position can increase according to the needs as well, thereby enhance the operational convenience and improve the action recognition efficiency.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Figure 1:
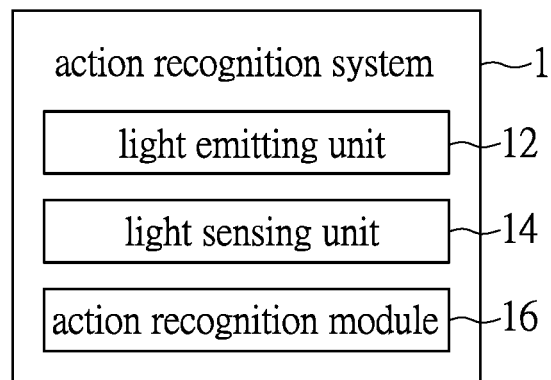
FIG. 1 is a block diagram illustrating an action recognition system provided in accordance to an exemplary embodiment of present disclosure.

Reference will now be made in detail to the exemplary embodiments of the present disclosure, examples of which are illustrated in the accompanying drawings. Wherever possible, the same reference numbers are used in the drawings and the description to refer to the same or like parts.

Figure 2:
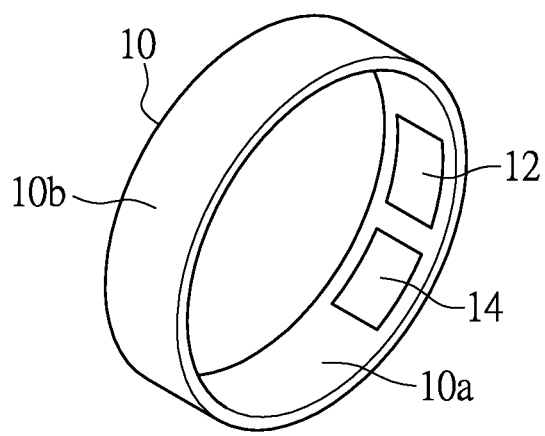
FIG. 2 is a perspective view illustrating an appearance of an annular body of an action recognition system provided in accordance to an exemplary embodiment of present disclosure.
Figure 3:
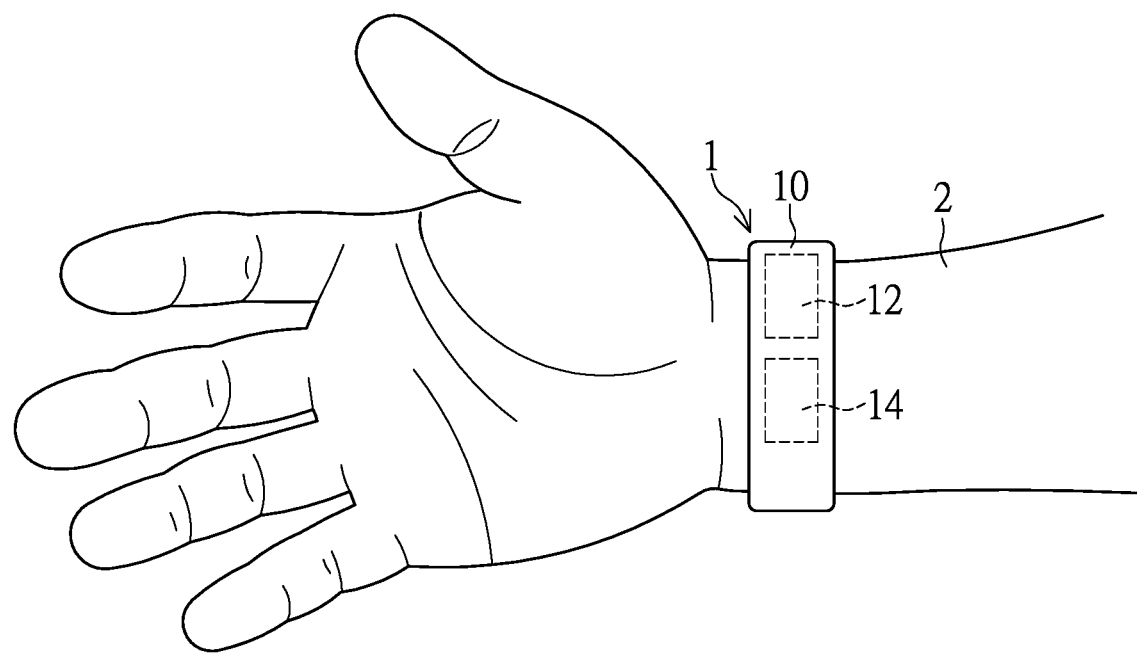
FIG. 3 is a diagram illustrating a usage example of an action recognition system provided in accordance to an exemplary embodiment of present disclosure.

Please refer to FIG. 1~FIG. 3 at the same time. FIG. 1 shows a block diagram illustrating an action recognition system provided in accordance to an exemplary embodiment of present disclosure. FIG. 2 shows a perspective view illustrating an appearance of an annular body of an action recognition system provided in accordance to the exemplary embodiment of present disclosure. FIG. 3 shows a diagram illustrating a usage example of an action recognition system provided in accordance to the exemplary embodiment of present disclosure. An action recognition system 1 includes at least one light emitting unit 12, at least one light sensing unit 14, and an action recognition module 16. The aforementioned components may be implemented by only hardware, or hardware accompanied by necessary firmware or software, and the present disclosure is not limited thereto. Additionally, the aforementioned components may be integrated into one single device or separately disposed, and the present disclosure is not limited thereto. It is worth noting that each of the aforementioned components may perform data transmission with each other in a wired or wireless manner, and the present disclosure is not limited thereto.

The action recognition system 1 of the present disclosure may be simply implemented by a wearable device or by a system integrally formed from a wearable device and another electronic device, however the present disclosure is not limited thereto. For the action recognition system 1 to easily form a wearable device, the action recognition system 1 must further include an annular body 10.

That is, the annular body 10 is one of main elements for the action recognition system 1 to form a wearable device. The annular body 10 as shown in FIG. 2 is configured to be worn on a movable part of a user. Particularly, the movable part herein may refer to any body part that moves by muscular contraction, e.g., hands or legs. However it should be understood that the preset disclosure does not limit the type of the movable part.

The appearance of the annular body 10 as illustrated in FIG. 2 includes an inner side 10a and an outer side 10b. The annular body 10 may be made of special material or a combination of a chain member having adjustable length and a chain buckle). The dimension of the annular body 10 can be configured based on the location and the dimension of the movable part such that the annular body 10 can be tightly and comfortable worn on the movable part and will not easily fall off. The present disclosure does not limit the exact implementation or design of the annular body 10. Those skilled in the art should be able to design the annular body 10 according to the practical operation and/or application requirement.

Those skilled in the art should understand that the shape of the wearable device formed of the action recognition system 1 is not necessary annular so long as the shape adopted for the main body of the wearable device can be easily worn on the movable part of the user while will not easily fall off the movable part. Hence, those skilled in the art can design the appearance of the annular body 10 according to the practical operation and/or application requirements of the applied product. The description provided herein below uses annular-shaped body for illustration only and the present disclosure is not limited to the example provided herein.

The following paragraphs uses FIG. 3 for illustration only and the present disclosure is not limited thereto. The annular body 10 in one embodiment can be worn on a wrist 2 of the user with the inner side 10a attached closely to the skin of the wrist 2. In the instant embodiment, the action recognition system 1 operatively generates a sensing signal in responsive to the optical detection of the muscular variation of the wrist 2 and determine an action of the user (e.g., the movement or motion of each finger, up/down bending or left/right movement of a palm, palm opening, hand grabbing or rotation operations and the like) according to the sensing signal.

The light emitting unit 12 is arranged in a manner that one end thereof is exposed on the inner side 10a of the annular body 10. The light emitting unit 12 is operable to emit a first light beam illuminating at least a portion of the wrist 2. More specifically, the light emitting unit 12 may be any type of semiconductor component capable of emitting visible or invisible light, e.g., light emitting diode. The present disclosure does not limit the exact type or exact implementation of the light emitting unit 12.

It is worth to note that the exact number used and the exact placement of the light emitting unit 12 on the annular body 10 shall not be limited to the illustrations provided by FIG. 2 and FIG. 3. For instance to accurately and quickly detect the muscular variation of the wrist 2, the light emitting unit 12 may be disposed or placed at a location with relatively more muscle tissues. For another instance, the exact number of the light emitting unit 12 used may be configured based on the practical operation and/or application, such as disposed sufficient number of the light emitting units 12 to detect the subtle muscular movement. The present disclosure does not limit the exact number and the exact placement of the light emitting unit 12 used.

The light sensing unit 14 is arranged in a manner such that one end thereof is also exposed on the inner side 10a of the annular body 10. The light sensing unit 14 is configured to sense or detect a second light beam generated as the first light beam reflected by at least a portion of the movable part and generate a light sensing signal, accordingly. In one embodiment, the light sensing unit 14 may be any type of photo-sensor, such as a Photoplethysmogram (PPG) sensor and the light sensing signal is generated by the PPG sensor. Particularly, the PPG sensor is operable to utilize the ability of a photo sensor absorbing the reflected light, and record the sensing signal generated responsive to the variation in the reflected light. As such, in comparison to the conventional SEMG sensor, the PPG sensor is operated by optically detecting the muscular variation and generate the light sensing signal accordingly, thus the sensing operation would not be easily interfered by the power source noise or EMI noise, henceforth the action recognition system 1 can provide more accurate and effective action recognition results.

It is worth to note that the exact number used as well as the exact placement of the light sensing unit 14 on the annular body 10 shall not be limited to the illustrations provided by FIG. 2 and FIG. 3. For instance, to accurately and quickly detect the second light beam generated as the first light beam reflected by the wrist 2, the light sensing unit 14 may be placed or arranged in proximity to or close to the position of the light emitting unit 12. The exact number of the light sensing unit 14 used may be increased according to the practical operation needs. The exact number employed for the light sensing unit 14 does not necessary have to be the same as the number of the light emitting units 12 used. The present disclosure further does not limit the exact type and exact implementation of the light sensing unit 14.

The action recognition module 16 is operable to identify and determine the action of the user based on the light sensing signal generated by the light sensing unit 14. It is worth to note that the action recognition module 16 may be built-in in the annular body 10 or disposed on another housing that is externally connected to the annular body 10. The present disclosure does not limit the exact placement of the action recognition module 16.

The action recognition module 16 in one embodiment may be implemented by any type of processor possessing sufficient processing capability for processing and analyzing the light sensing signal received, and to compute and establish a characteristic vector accordingly thereafter assisting the action recognition operation. Each characteristic vector herein corresponds to an action of the user. The relationship between each characteristic vector and the respective action may be recorded in a lookup table. The lookup table may be stored in a built-in memory of the action recognition module 16 or store in a memory device (not shown) connected externally to the action recognition module 16 for the action recognition module 16 to access and perform lookup operation. It is worth to note that the present disclosure does not limit the exact implementation method and/or algorithm for action recognition and those skilled in the art should be able to design the action recognition module 16 based on practical operation or application requirements.

To put it concretely, after the action recognition module 16 processes and analyzes the light sensing signal received, the action recognition module 16 establishes a characteristic vector, obtains the action corresponding to the characteristic vector to be a firmly grasping motion using the pre-stored lookup table, and determines that the action of the user is "hand grasping". In another embodiment, supposed the characteristic vector established by the action recognition module 16 after processing and analyzing the light sensing signal received to correspond to a V-sign gesture (e.g., the fingers are held in a V-sign gesture) using the pre-stored lookup table, the action recognition module 16 operatively determine that the action of the user is the "V-sign gesture". The above identifying actions using lookup table are provided for illustration only and the present disclosure is not limited thereto.

In one embodiment, the action recognition system 1 may further determine the displacement of the wrist 2 and/or the rotation direction and the associated rotation angle for increase the accuracy of the action recognition operation. Please refer to FIG. 4, which shows a block diagram illustrating an action recognition system provided in accordance to another exemplary embodiment of present disclosure. An action recognition system 4 in comparison to the action recognition system 1 further includes at least one of an accerlometer module 40 and a gyro module 42. The accerlometer module 40 and the gyro module 42 are operable to perform data transmission with the action recognition module 16 in a wired or wireless manner. Similarly, the accerlometer module 40 and the gyro module 42 may be built-in in the annular body 10 or disposed on another housing (not shown) that is externally connected to the annular body 10. The present disclosure does not limit the exact placement of the accerlometer module 40 and the gyro module 42.

More specifically, the accelerometer module 40 is operable to determine a displacement of the wrist 2. The gyro module 42 is operable to determine a rotation direction and a rotation angle of the wrist 2. The action recognition module 16 thus is operable to precisely determine the action of the user according to the light sensing signal and at least one of the displacement, the rotation direction and the rotation angle, the actions to be identified henceforth can be more diversified. Additionally, those skilled in the art should be able to design an appropriate movement measuring method and data analyzing method for the accerlometer module 40 and the gyro module 42 based on practical operation and/or application needs, and further descriptions are hereby omitted.

Addition, since the operation of the light sensing unit 14 is to detect or collect the light beam reflecting muscular variation with a photo sensing element and generate the light sensing signal, accordingly. Thus, the light sensitivity requirement for the light sensing unit 14 is relatively high. Hence, the action recognition system 4 further can include a light source controller 44. The light source controller 44 is disposed on the annular body 10, and the light source controller 44 is electrically connected to the light emitting unit 12 for controlling the light intensity (or the brightness) of the first light beam emitted by the light emitting unit 12.

Figure 5:
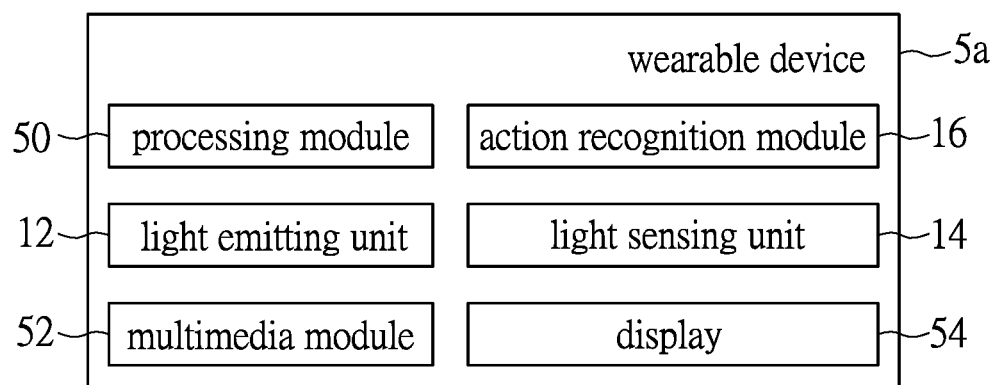
FIG. 5 is a block diagram illustrating a wearable device comprising of an action recognition system provided in accordance to another exemplary embodiment of present disclosure.
Figure 6:
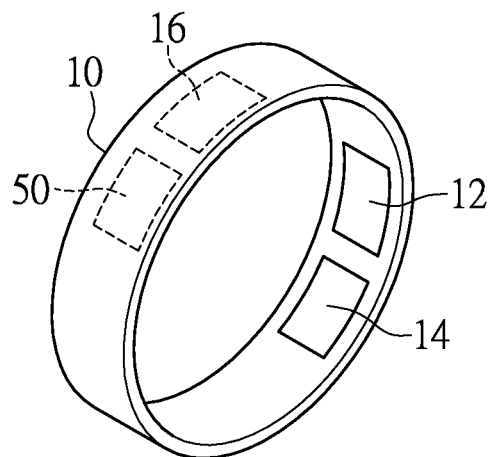
FIG. 6 is a perspective view illustrating an appearance of a wearable device comprising of an action recognition system provided in accordance to another exemplary embodiment of present disclosure.

Those skilled in the art should be able to generalize several implementations for the action recognition system 1 based on the disclosure herein above. As previously described, the action recognition system may be simply implemented by a wearable device or by a system integrally formed of a wearable device and another electronic device. Please refer to FIG. 5 in conjunction with FIG. 6. FIG. 5 shows a block diagram illustrating a wearable device formed of an action recognition system provided in accordance to another exemplary embodiment of present disclosure. FIG. 6 shows a perspective view illustrating an appearance of a wearable device formed of an action recognition system provided in accordance to another exemplary embodiment of present disclosure. It shall be noted that for ease of reference, the same reference number will be given to parts in FIG. 5 and FIG. 6 that are the same or similar to FIG. 1, and further descriptions associated with the same or similar parts will be omitted.

To put it concretely, the annular body 10, the light emitting unit 12, the light sensing unit 14, and the action recognition module 16 of an action recognition system 5 in the instant embodiment form a wearable device 5a. The action recognition system 5 further includes a processing module 50, which is also disposed in the wearable device 5a. The processing module 50 is configured to operatively perform a function that corresponds to the action of the user identified by the action recognition module 16.

Since each action made by the user represents a function to be executed or performed by the wearable device 5a, thus, the action recognition module 16 transmits the action determination result to the processing module 50 after determined the action of the user in such a manner that enables the processing module 50 to drive the wearable device 5a to perform or execute the function corresponding to the action determination result.

In one embodiment, the wearable device 5a may further have other application module(s) such as a multimedia module 52 disposed therein. The wearable device 5a may further has a display 54 disposed thereon for selectively display related multimedia information. Such that, the wearable device 5a can directly determine the action of the user with the action recognition module 16 while executing a music playback application of the multimedia module 52 and control the multimedia module 52 to perform the corresponding function (e.g., playback the next or previous track, page turning operation, call receiving or dialing operation, pause or stop current track, fast forward or rewind current playing track, volume control, or the like) based on the action determination result. In short, the descriptions provided herein above describing the method for causing the processing module 50 to drive the wearable device 5a to perform a function that corresponds to the action of the user determined are for illustration only, and the present disclosure is not limited thereto.

Figure 7:
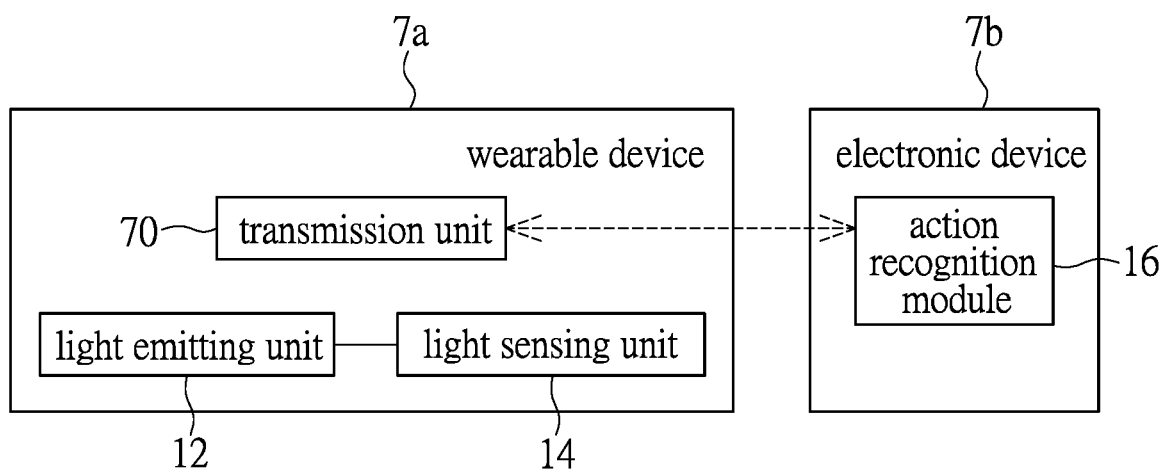
FIG. 7 is a block diagram illustrating a wearable device comprising of an action recognition system provided in accordance to another exemplary embodiment of present disclosure.
Figure 8:
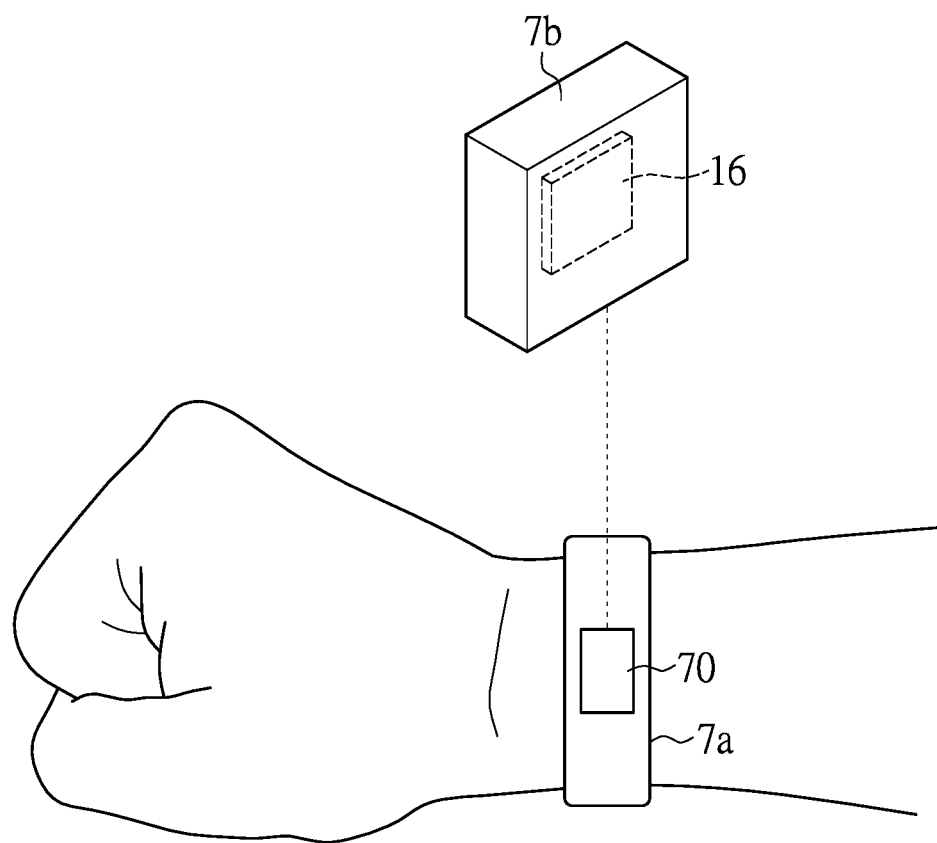
FIG. 8 is a diagram illustrating a usage example of an action recognition system provided in accordance to another exemplary embodiment of present disclosure.

Please refer to FIG. 7 in conjunction with FIG. 8. FIG. 7 shows a block diagram illustrating a wearable device comprising an action recognition system provided in accordance to another exemplary embodiment of present disclosure. FIG. 8 shows a diagram illustrating a usage example of an action recognition system provided in accordance to another exemplary embodiment of present disclosure. It shall be noted that for ease of reference, the same reference number will be given to parts in FIG. 7 and FIG. 8 that are the same or similar to FIG. 1, and further descriptions associated with the same or similar parts will be omitted.

Specifically, an action recognition system 7 further includes a transmission unit 70. The transmission unit 70 is operable to transmit the light sensing signal to the action recognition module 16 in a wired or wireless manner. The annular body 10, the light emitting unit 12, the light sensing unit 14, and the transmission unit 70 form a wearable device 7a. In comparison to the wearable device 5a of FIG. 5, the wearable device 7a does not include the action recognition module 16.

Particularly, the action recognition system 7 further includes an electronic device 7b having the action recognition module 16. The electronic device 7b may be any electronic product having processing capability include but not limited to a smart handheld device with communication capability, a tablet, a desktop, laptop, or a multimedia playback device, and the present disclosure is not limited thereto.

The transmission unit 70 of the wearable device 7a is configured to transmit the light sensing signal to the action recognition module 16 of the electronic device 7b. Thus, differ from the wearable device 5a depicted in FIG. 5, the wearable device 7a does not actively determine the action of the user, instead, the action of the user in the instant embodiment is determined by the built-in action recognition module 16 of the electronic device 7b. Hence, the electronic device 7b is configured to perform the function corresponding to the action of the user after the action recognition module 16 identified the instant action of the user.

In an embodiment, where the electronic device 7b is a multimedia playback device, and every action made by the user corresponds a function to be executed by the electronic device 7b, such as playback the previous or next track, stop playing the current track, fast forward or fast rewind the current track, volume control and the like. Thus, after the transmitting unit 70 of the wearable device 7a transmits the light sensing signal to the action recognition module 16 of the electronic device 7b, the action recognition module 16 operatively determines the action of the user according to the light sensing signal and drives the electronic device 7b to perform a corresponding function based on the action determination result. The example provided herein describing the methodology for configuring the action recognition module 16 to drive the electronic device 7b to perform or execute the corresponding function merely serve as an illustration, and the present disclosure is not limited thereto.

To sum, the action recognition system provided by the present disclosure operated by optically detecting the muscular variation and generating a sensing signal, accordingly, therefore would not easily affected by the power source noise and/or EMI noise, moreover the number of measuring positions can be increased according to the operation and/or application needs, thereby increase operational convenience as well as the accuracy of action recognition operation.

To further elaborates on the operation process of the action recognition system, the preset disclosure further provides an implementation of the action recognition method for the action recognition system. Please refer to FIG. 9, which shows a flowchart diagram illustrating an action recognition method provided in accordance to an exemplary embodiment of present disclosure. The action recognition method depicted in FIG. 9 can be used and executed by any of the action recognition system illustrated by FIG. 1, FIG. 4, FIG. 5, and FIG. 7. Hence for better understandings, please refer to FIG. 9 in conjunction with FIG. 1, FIG. 4, FIG. 5, and FIG. 7. Additionally, detail descriptions on the steps that have been provided in the previous embodiment, hence details are omitted for simplicity and only the main ideas are provided.

In Step S901, a light emitting unit is arranged and configured to emit a first light beam onto at least of a portion of a movable part of a user. The light emitting unit is arranged such that one end of the light emitting unit is exposed on an inner side of an annular body. In Step S902, a light sensing unit is arranged and configured to detect a second light beam generated as the first light beam reflected by the at least a portion of the movable part reflecting and generate a light sensing signal, accordingly. The light sensing unit is also arranged to have one end thereof exposed on an inner side of an annular body. In Step S905, an action recognition module is further utilized to determine an action of a user according to the light sensing signal.

Figure 9:
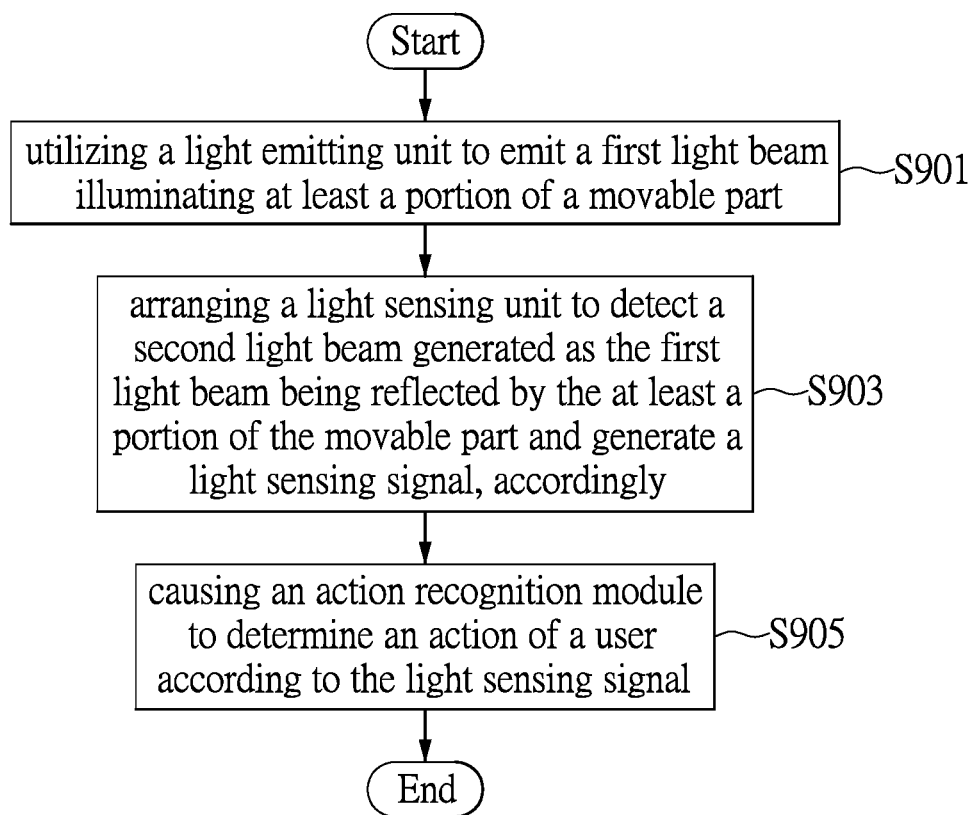
FIG. 9 is a flowchart diagram illustrating an action recognition method provided in accordance to an exemplary embodiment of present disclosure.
Figure 10:
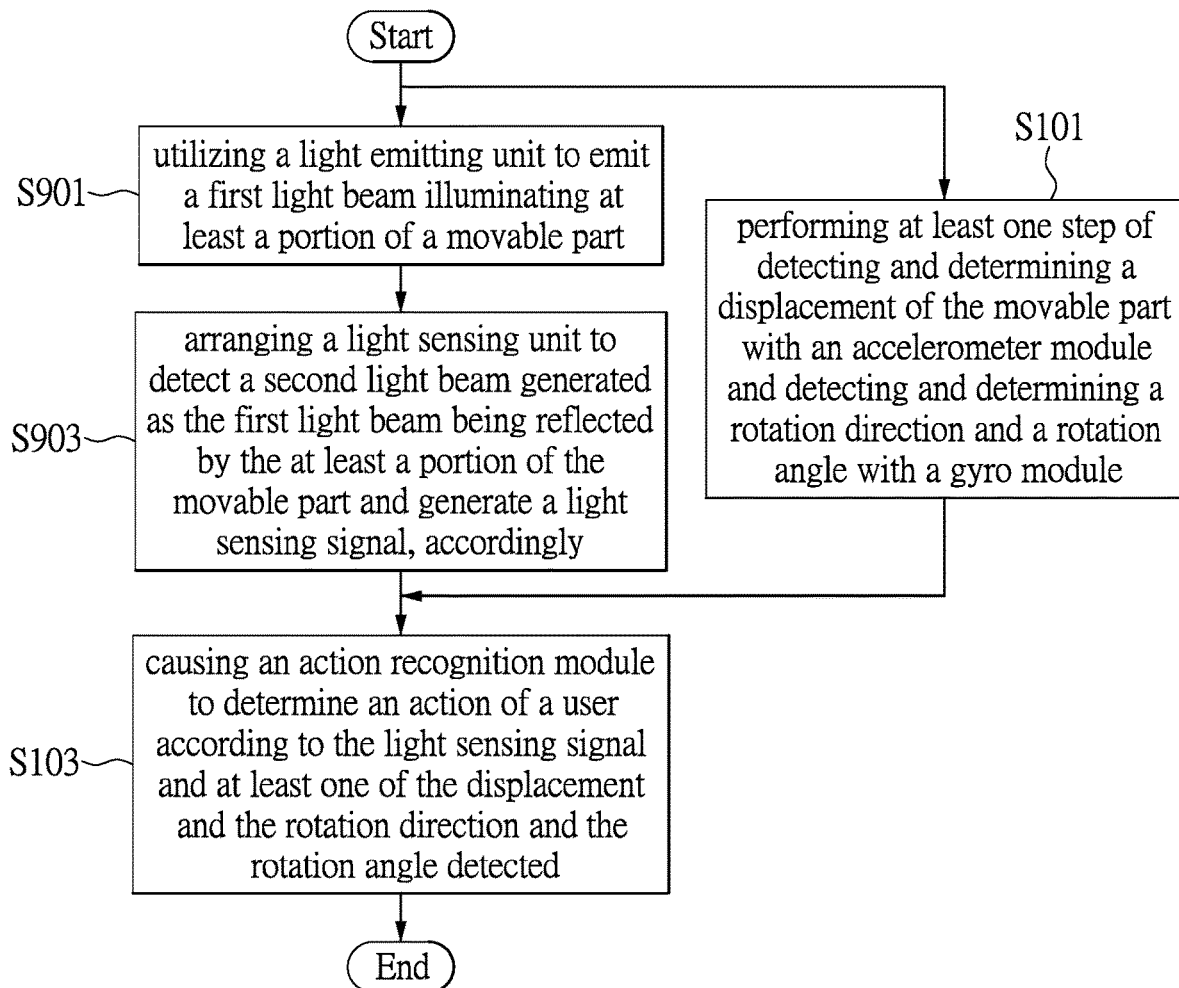
FIG. 10 is a flowchart diagram illustrating an action recognition method provided in accordance to another exemplary embodiment of present disclosure.

Next, please refer to FIG. 10, which shows a flowchart diagram illustrating an action recognition method provided in accordance to another exemplary embodiment of present disclosure. It shall be noted that for ease of reference, the same reference number will be given to steps in FIG. 10 that are identical to the steps depicted in FIG. 9 and further descriptions are omitted for simplicity. The action recognition method of FIG. 10 further takes the displacement information, the rotation direction and the associated rotation angle of the movable part into consideration in the process of identifying the action of the user. However, FIG. 10 merely depict an implementation of the action recognition method and the present disclosure is not limited thereto.

Figure 4:
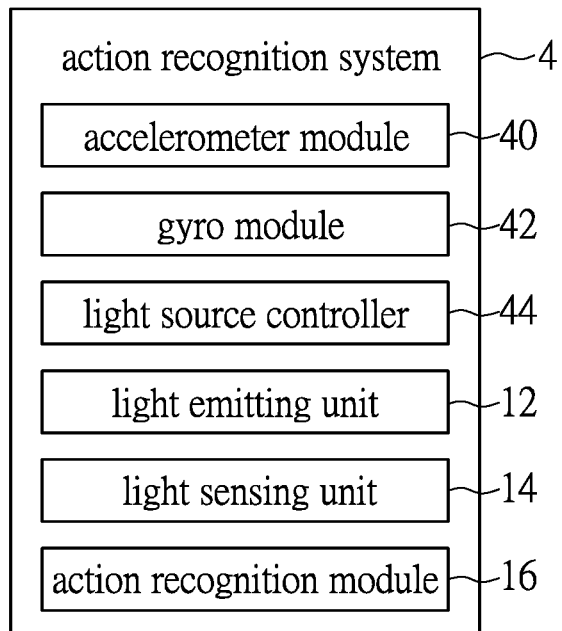
FIG. 4 is a block diagram illustrating an action recognition system provided in accordance to another exemplary embodiment of present disclosure.

The action recognition method provided in FIG. 10 can be executed by the action recognition system 4 of FIG. 4. Therefore, in order to obtain a better understanding, please refer to FIG. 10 in conjunction with FIG. 4. Additionally, detail descriptions on the steps that have been provided in the previous embodiments, hence details are omitted for simplicity and only the main ideas are provided.

The steps S901 and S903 are the same as the Steps S901 and S903 depicted in FIG. 9 and hence further description are hereby omitted. In Step S101, at least one step or operation of driving an accelerometer module to detect and determine the displacement of the movable part and driving a gyro module to detect a rotation direction and a rotation angle with gyro module is performed. In Step S103, an action recognition module is arranged and configured to determine an action of a user according to the light sensing signal and at least one of the displacement and the rotation direction and the rotation angle detected.

The action recognition system may be simply implemented by a wearable device or implemented by a wearable device and another electronic device. Example implementations of action recognition method for action recognition systems depicted in FIG. 5 and FIG. 7 are provided herein below, however it shall be noted that the present disclosure is not limited thereto.

Figure 11:
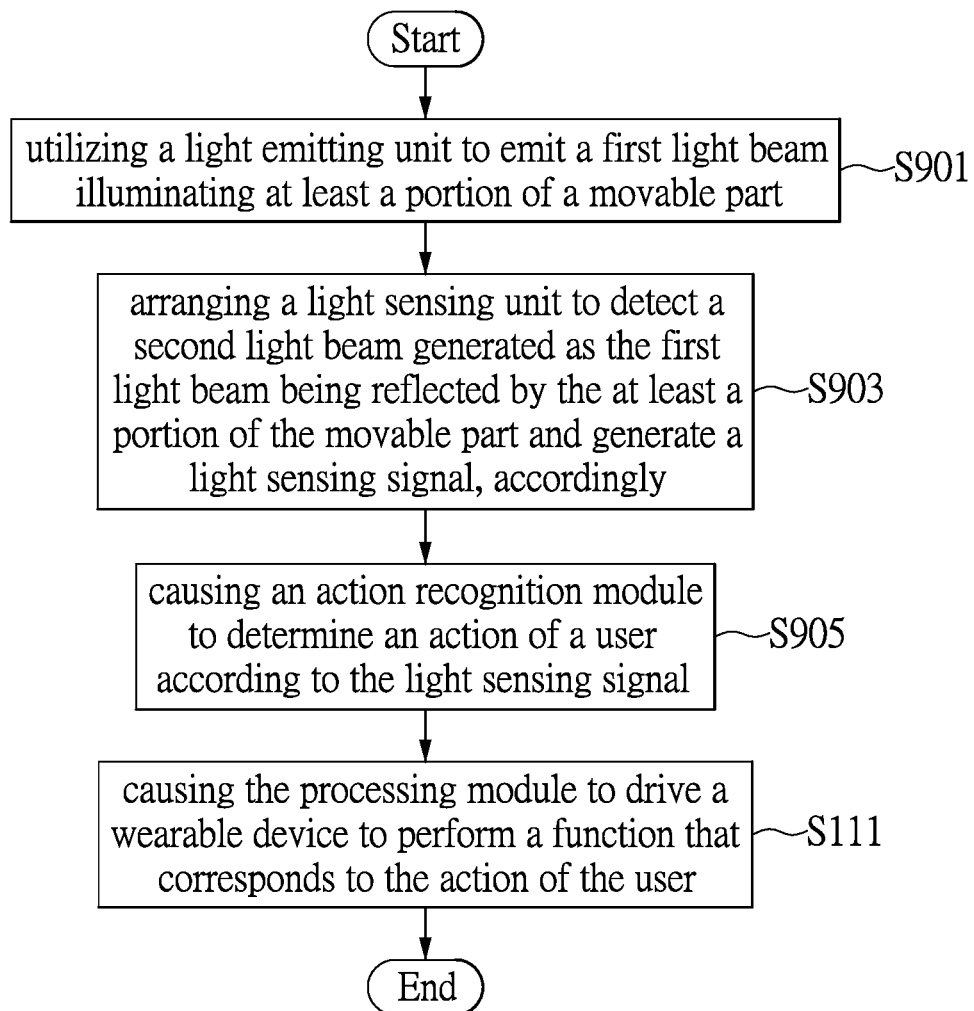
FIG. 11 is a flowchart diagram illustrating an action recognition method provided in accordance to another exemplary embodiment of present disclosure.

Please refer to FIG. 11, which shows a flowchart diagram illustrating an action recognition method provided in accordance to another exemplary embodiment of present disclosure. The action recognition method provided in FIG. 11 can be executed by the action recognition system 5 of FIG. 5. Therefore, in order to obtain a better understanding, please refer to FIG. 11 in conjunction with FIG. 5. Additionally, detail descriptions on the steps that have been provided in the previous embodiments, hence details are omitted for simplicity and only the main ideas are provided.

The steps S901, S903, and S905 of FIG. 11 are the same as the Steps S901, S903, and S905 depicted in FIG. 9 and hence further description are hereby omitted. In Step S111, the processing module is configured to drive a wearable device to perform a function that corresponds to the action of the user.

Figure 12:
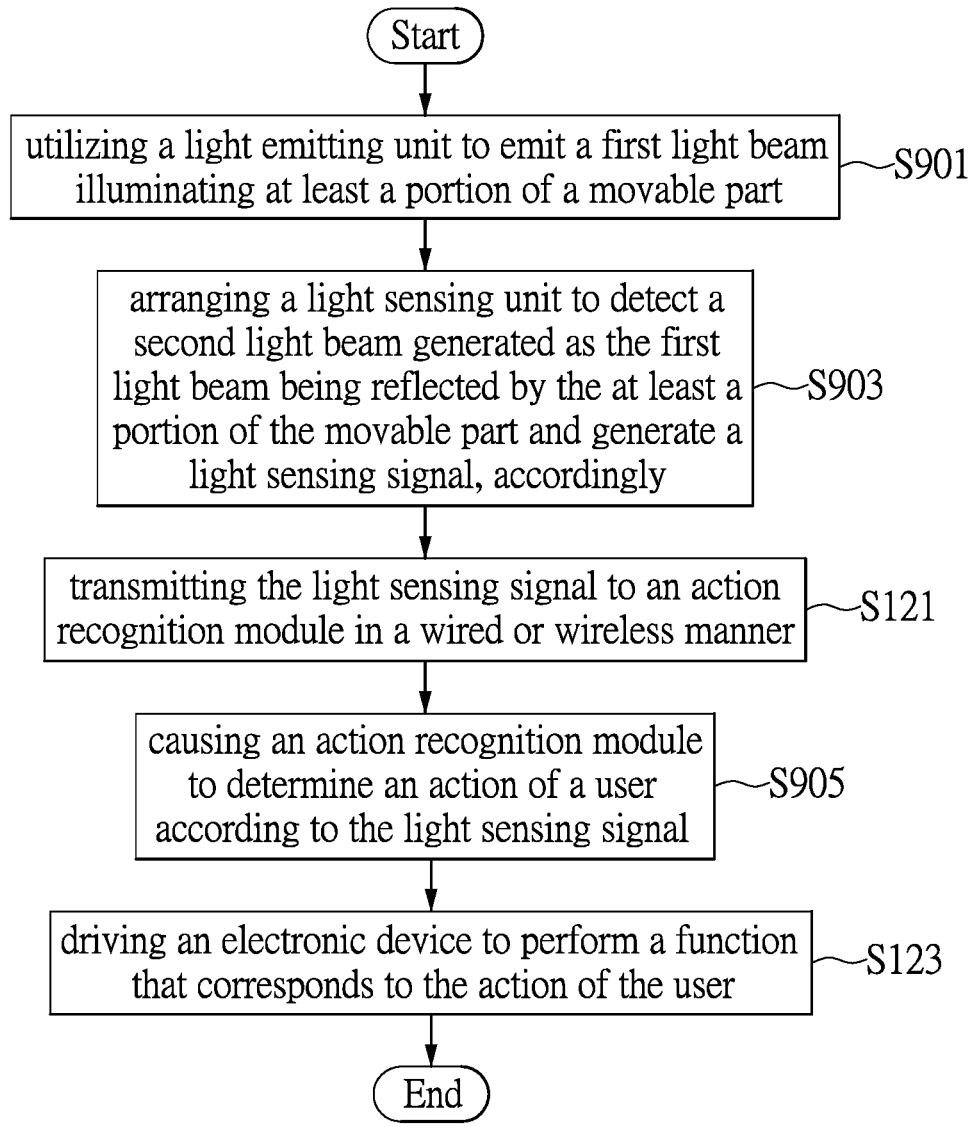
FIG. 12 is a flowchart diagram illustrating an action recognition method provided in accordance to another exemplary embodiment of present disclosure.

Please refer to FIG. 12, which shows a flowchart diagram illustrating an action recognition method provided in accordance to another exemplary embodiment of present disclosure. The action recognition method provided in FIG. 12 can be executed by the action recognition system 7 of FIG. 7. Therefore, in order to obtain a better understanding, please refer to FIG. 12 in conjunction with FIG. 7. Additionally, detail descriptions on the steps that have been provided in the previous embodiments, hence details are omitted for simplicity and only the main ideas are provided.

The steps S901, S903, and S905 of FIG. 12 are the same as the Steps S901, S903, and S905 depicted in FIG. 9 and hence further description are hereby omitted. In Step S121, a transmission unit is driven to transmit the light sensing signal to the action recognition module of an electronic device in a wired or wireless manner. In Step S123, the electronic device is configured to operatively perform a function that corresponds to the action of the user In summary, exemplary embodiments of the present disclosure provides an action recognition system and method thereof, which operated mainly by optically detecting the muscle variation of a user and generating a sensing signal, accordingly, thereby eliminating the impact of EMI interferences and power source noises. Moreover, the number of muscle measuring or detection positions can increase as well, thereby enhance the operational convenience and improve the action recognition efficiency.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. An action recognition system, comprising:
a body configured to be disposed on a movable part of a user;
at least one light emitting unit disposed on an inner side of the body, the light emitting unit operable to emit a light beam illuminating at least a portion of the movable part;
at least one light sensing unit disposed on the inner side of the body, the light sensing unit operable to sense the light beam reflected by the at least a portion of the movable part and to generate a light sensing signal in responsive to a muscular variation of the movable part of the user; and
an action recognition module, operable to process and analyze the light sensing signal received to establish a characteristic vector in responsive to the muscular variation, and to identify and determine an action of the user according to the processed light sensing signal by performing an operation, wherein the operation includes obtaining the action corresponding to the characteristic vector by using an information table, the information table records a relationship between the character vector and the respective action, and the action includes a movement or a motion of each finger, up bending, down bending, left movement, and right movement of a palm, palm opening, hand grabbing or hand rotation operation; and
a processing module disposed in a wearable device, the processing module operable to cause the wearable device to perform a function that corresponds to the action of the user.

2. The action recognition system according to claim 1, wherein the light emitting unit is a light emitting diode (LED).

3. The action recognition system according to claim 1, wherein the light sensing unit is a Photoplethysmogram (PPG) sensor.

4. The action recognition system according to claim 1, further comprising a light source controller disposed on an annular body, the light source controller coupled to the light emitting unit for controlling the light intensity of the light beam emitted by the light emitting unit.

5. The action recognition system according to claim 1, further comprising at least one of an accelerometer module operable to determine a displacement of the movable part, and a gyro module operable to determine a rotation direction and a rotation angle associated with the movable part, the action recognition module operatively determining the action of the user according to the light sensing signal and at least one of the displacement and the rotation direction and the rotation angle.

6. The action recognition system according to claim 1, wherein the body, the light emitting unit, the light sensing unit, and the action recognition module form the wearable device.

7. The action recognition system according to claim 1, further comprising a transmission unit, the transmission unit operable to transmit the light sensing signal to the action recognition module in a wired or wireless manner, the body, the light emitting unit, the light sensing unit and the transmission unit form the wearable device, wherein the action recognition module is disposed outside the wearable device.

8. The action recognition system according to claim 7, further comprising an electronic device having the action recognition module disposed therein, and the electronic device configured to perform the function that corresponds to the action of the user.

* * * * *